United States Patent [19]

Kingston

[11] Patent Number: 5,521,582
[45] Date of Patent: May 28, 1996

[54] ALARM SYSTEM

[76] Inventor: John E. Kingston, 49 Allestree Drive, Scartho, Grimsby, South Humberside DN33 3DX, United Kingdom

[21] Appl. No.: 342,427

[22] Filed: Nov. 18, 1994

Related U.S. Application Data

[63] Continuation-in-part of Ser. No. 941,101, Oct. 19, 1992, abandoned.

[30] Foreign Application Priority Data

Apr. 21, 1990 [GB] United Kingdom ............... 9008992

[51] Int. Cl.⁶ .................................................. G08B 1/08
[52] U.S. Cl. .................. 340/539; 340/531; 340/573; 368/11; 368/12; 379/37; 455/89
[58] Field of Search ............................. 340/539, 531, 340/691, 692, 573, 534; 455/38.1, 38.2, 228, 89; 379/37–40; 381/111, 122; 368/1, 10–13

[56] References Cited

U.S. PATENT DOCUMENTS

| | | | |
|---|---|---|---|
| 4,056,815 | 11/1977 | Anderson | 340/539 |
| 4,068,097 | 1/1978 | Verriest | 379/38 |
| 4,092,643 | 5/1978 | Stolarczyk | 340/539 |
| 4,510,350 | 4/1985 | Wagner et al. | 379/38 |
| 4,819,860 | 4/1989 | Hargrove et al. | 340/593 |
| 4,876,710 | 10/1989 | Reed et al. | 379/58 |
| 4,906,972 | 3/1990 | Spencer | 340/534 |
| 5,119,072 | 6/1992 | Hemingway | 340/539 |
| 5,159,315 | 10/1992 | Schultz et al. | 340/539 |

FOREIGN PATENT DOCUMENTS

| | | |
|---|---|---|
| 2425230 | 5/1978 | France . |
| 2632899 | 6/1977 | Germany . |
| 0810730 | 3/1959 | United Kingdom . |
| 1543441 | 4/1979 | United Kingdom . |

*Primary Examiner*—Donnie L. Crosland
*Attorney, Agent, or Firm*—Ira S. Dorman

[57] ABSTRACT

A signalling device to be worn on the person includes an emergency button (2) which triggers an internal transmitter to transmit an encoded identification signal followed by audio signals derived from sounds picked up by a microphone (3). The transmitted signals are picked up by a control box (21) containing a radio receiver which encodes the signals and commands an alarm box (24) to send out an audible and/or visual warning. Such warnings alternate with periods in which the alarm box broadcasts sounds picked up by the microphone (3).

7 Claims, 4 Drawing Sheets

ALARM SYSTEM

CROSS REFERENCE TO RELATED APPLICATION

This application is a continuation-in-part of application Ser. No. 07/941,101, filed Oct. 19, 1992, now abandoned.

TECHNICAL FIELD OF THE INVENTION

This invention relates to personal alarm systems for indicating when a user is in distress or requires assistance.

BACKGROUND ART

GB 810 730 discloses a small radio transmitter which is worn on the wrist and transmits an audio signal to reveal the wearer's position if he/she is accidentally buried. In todays crowded urban environment however, the transmission of an audio signal alone would result in a high risk of false alarms.

It is also known from GB 1 543 441, U.S. Pat. No. 4,510,350 and U.S. Pat. No. 4,819,860 to provide a wrist mounted transmitter which transmits a digital identification code. In the case of U.S. Pat. No. 4,510,350 the transmitter is triggered to send a prerecorded digitised vocal message over the telephone network by simultaneous depression of two buttons.

SUMMARY OF THE INVENTION

Whilst the transmission of an encoded signal would reduce or eliminate the risk of false alarms, the present invention is based on the premise that many people would find it more reassuring to know that their cries of help would be heard if they should come face to face with an aggressor for example. In addition, it is believed that may people would tend to react quicker to cries of help than they would to an alarm bell or siren.

The present invention proposes that, when activated, a personal alarm signalling device transmits audio signals which convey sounds picked up by a microphone, together with an encoded identification signal.

To ensure efficient identification of the signalling device the identification signal is preferably repeated numerous times before the audio signals are transmitted.

The identification signal may initiate an audible and/or visual alarm which alternates with the public broadcasting of the sounds which are picked up by the microphone. Alternatively, the identification signal may initiate a telephone call to a monitoring base to which the audio signals are then sent.

BRIEF DESCRIPTION OF THE DRAWINGS

The invention is exemplified in the accompanying drawings, in which.

DETAILED DESCRIPTION OF THE DRAWINGS

The alarm system includes a signalling device 41 (FIG. 1), a control box 21 (FIG. 4) including a cradle 30 for receiving the signalling device, and an alarm box 24.

Figure 1:
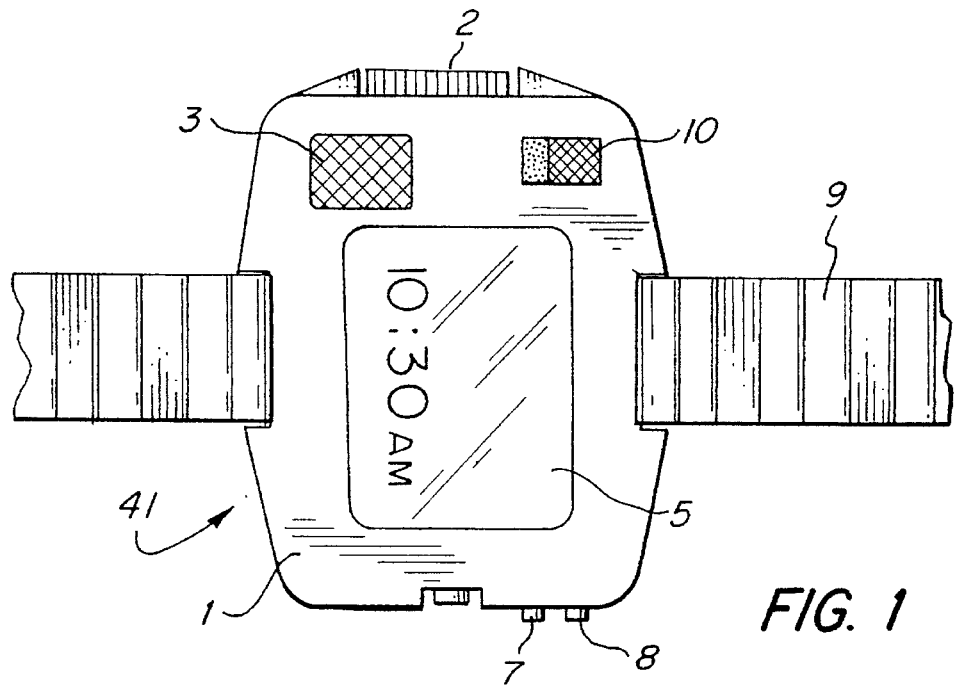
FIG. 1 is a front view of an alarm signalling device for use in an alarm system in the invention.

Referring to FIG. 1, the signalling device 41 comprises a housing 1 of durable plastics having an emergency button 2 mounted in its wall. The front face of the housing includes a microphone 3 and a liquid crystal display panel 5 which can give a time readout as in a digital watch. On the side of the housing there are two "set" buttons 7 and 8. The housing is secured to a wrist band 9, but the housing may also be adapted to be worn anywhere on the body, for example suspended on a loop worn around the neck, on a belt or key ring, or to be attached to the clothing by safety pins, a spring clip, or more secure means. The display panel 5 and buttons 7 and 8 could be omitted if desired.

Figure 2:
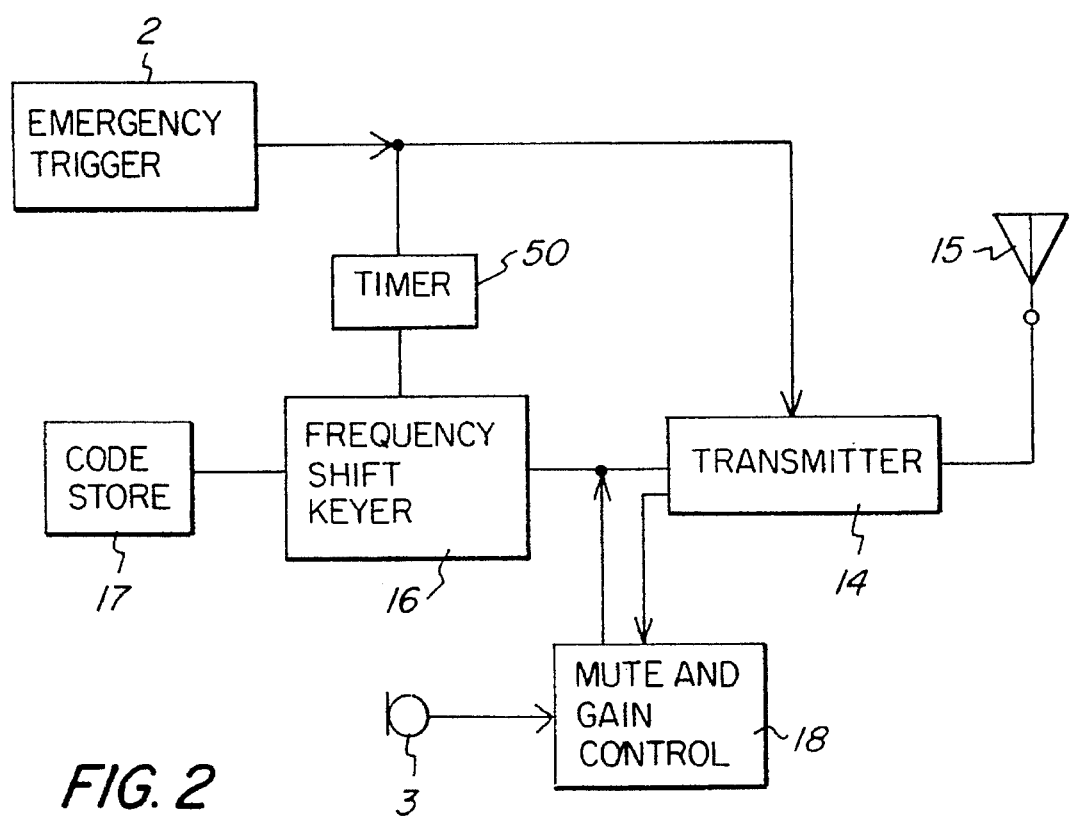
FIG. 2 is a block circuit diagram of the signalling device.

Referring now to FIG. 2, the housing contains a microtransmitter 14 which generates a low power radio signal in the 49 MHz region, although other frequencies could be used. The signal is transmitted from a wire antenna 15 which can be incorporated into the wrist band 9, or the loop if worn around the neck, or internally within the housing. The transmitter can be powered from internal rechargeable batteries (not shown) which can be re-charged by conventional means or, by placing the signalling device in the cradle 30, the batteries can be re-charged from the control box 21 via suitable electrical contacts provided on the signalling device and the cradle. The transmitter could also be powered by non-rechargeable batteries if required. An audio and/or visual battery condition indicator 10 (FIG. 1) may be provided on the signalling device to inform the user when the batteries are low and require recharging or replacing.

Referring back to FIG. 2, a frequency shift keying device 16 is arranged to modulate the transmitter with a binary identification code held in shift registers 17. The method and type of coding depends upon the level of security demanded of the system. The code may be set by the user by means of the buttons 7 and 8, which can also be used for setting the watch, or the code could be automatically transferred from the control box into the shift registers when the signalling device is placed in the cradle 30. The code could also be set internally via miniature switches or links on the printed circuit board during manufacture. In addition to an identification code, further codes could be transmitted, for example to enable a user to signal which of the emergency services is required, e.g. fire, police or ambulance, via the public telephone system. The transmitter can also be phase modulated by the audio signals from the microphone 3 via an automatic gain control circuit 18.

The emergency trigger button 2 is arranged to operate the keying device 16 via a timer 50 so that the identification code is generated for an initial period set by the timer. Operation of the button 2 also energises the transmitter 13, which remains on to transmit audio signals from the microphone 3 following transmission of the identification code.

Figure 3A:
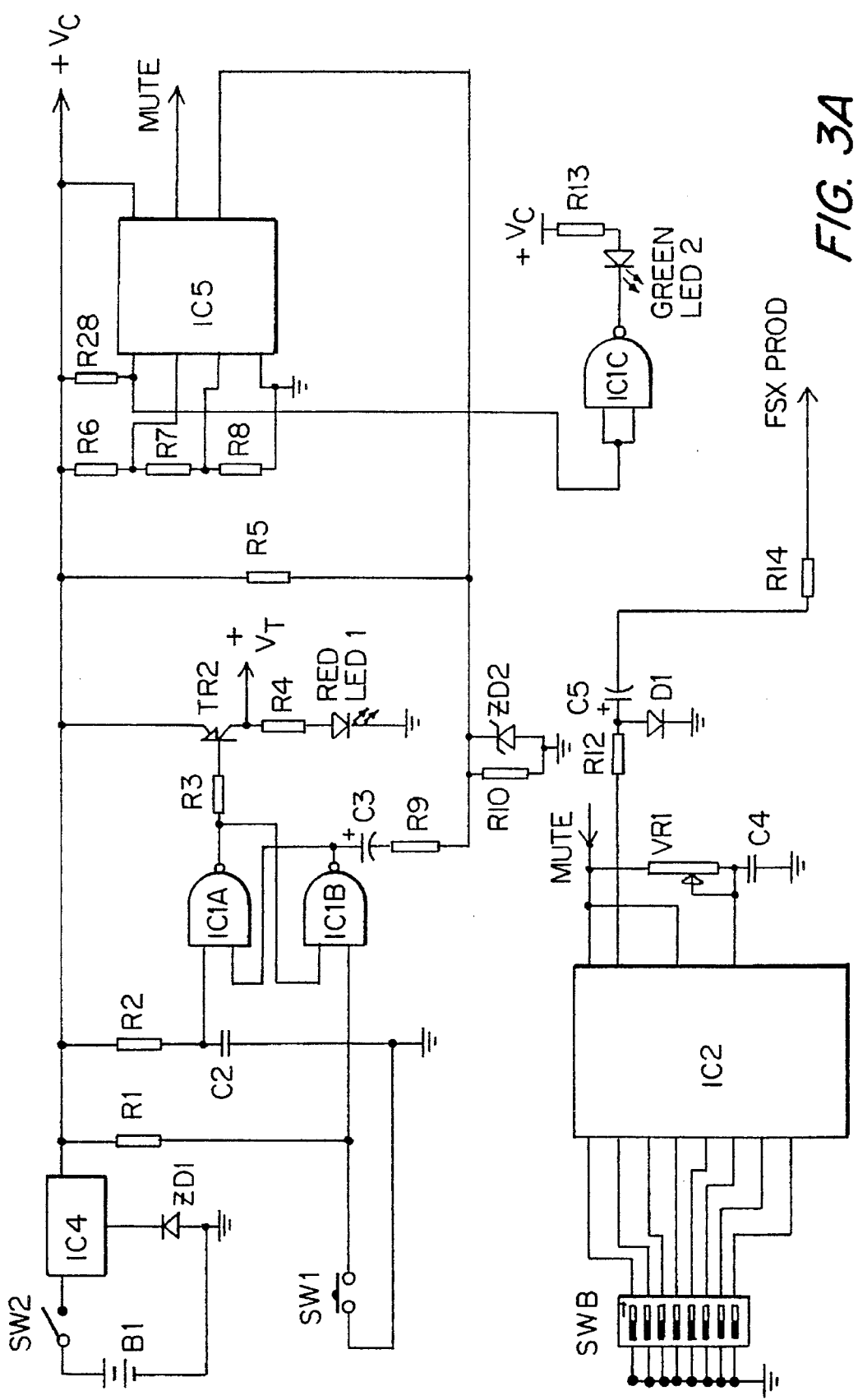
FIGS. 3A and 3B are detailed circuit diagrams of one form of the signalling device.
Figure 3B:
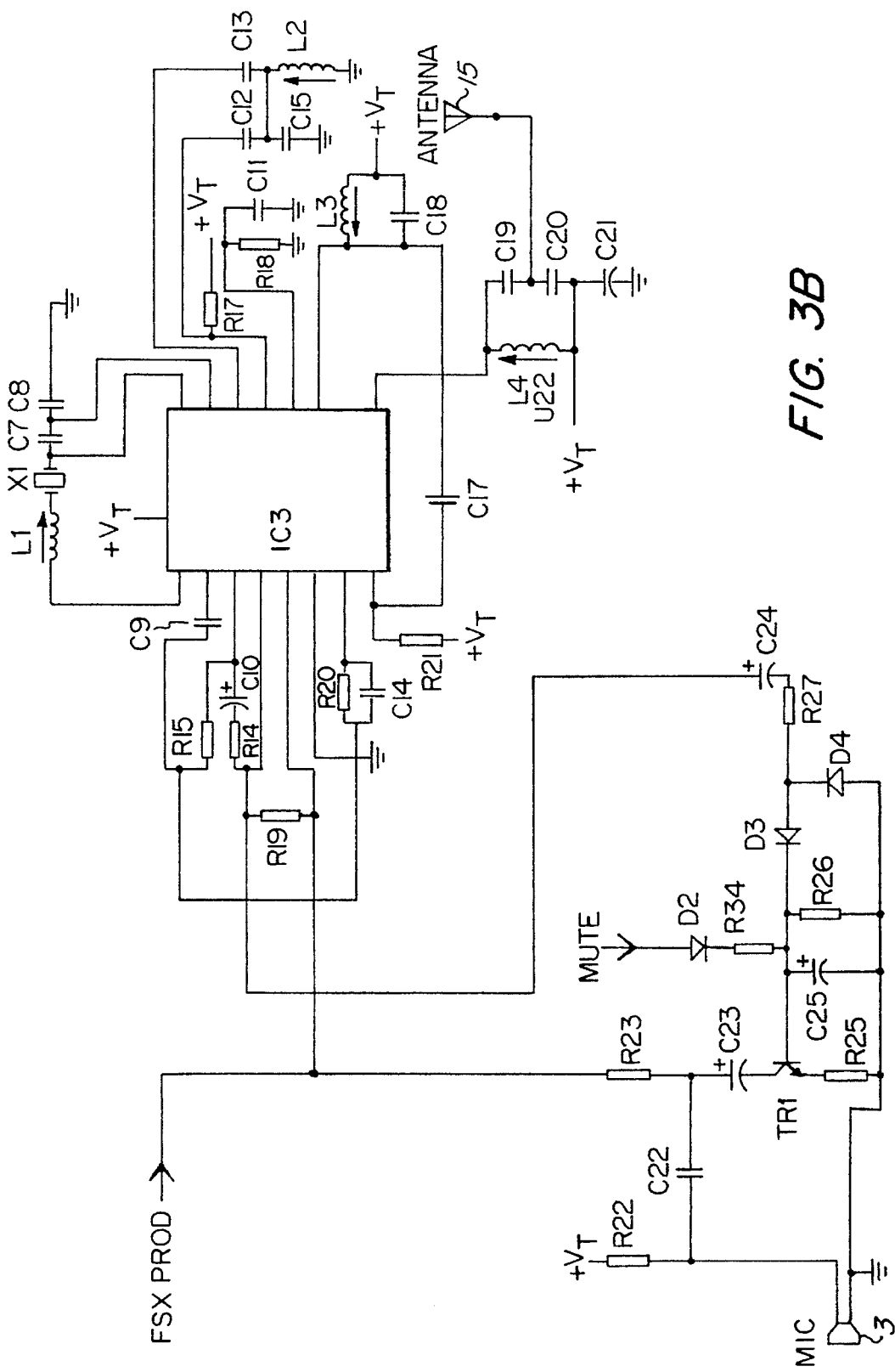

FIGS. 3A and 3B show a detailed circuit diagram of a preferred form of the signalling device of FIG. 2. Power from a battery B1 is supplied via on/off switch SW2 and a 78L05 voltage regulator chip IC4. An input of latch IC1B (type 4093) is normally held high by resistor R1 but a momentary depression of emergency trigger switch SW1 operates the latch to send a voltage pulse via C3 and R9 to an input of IC5 (type ICL7665) causing its output to go high for a period of about 5 seconds until capacitor C3 becomes fully charged. The voltage from IC5 powers a UM3750 encoded/frequency shift keyer chip IC2, which generates a 4×12 bit digital word identification signal which can be preset using a code store in the form of a switch bank SWB. The encoded digital signal is repeated many times and passes via R12, C5 and R14 to frequency shift modulate transmitter chip IC3, type MC2833—FIG. 1B.

The amplified audio signal is tapped off from the transmitter IC3 and fed via C24 and R27 to be rectified by D3, D4. The resulting rectified voltage turns on transistor TR1 which shunts any audio input from microphone 3 to earth via C23.

Returning to FIG. 3A, the voltage pulse appearing at the output of latch IC1B triggers a second latch IC1A causing its output to latch low and cause transistor TR2 to conduct. TR2 supplied power to the transmitter IC3 to generate a radio frequency signal and causes a red warning diode LED 1 to light.

When the code generator IC2 is turned off at the end of the pulse supplied by IC5, audio signals can pass from the microphone 3 via C22 and R23 to modulate the transmitter IC3. The amplified audio signals rectified by D3 and D4 cause transistor TR1 to conduct on audio signal peaks, providing automatic gain control. Once latch IC1A has been triggered as described, it holds the transmitter IC3 in an "on" condition until removal of the supply voltage by the main power switch SW2.

IC5 also acts as a battery condition monitor since a fall in the regulated supply voltage causes it to send a high output to inverter IC1C which turns on a green battery condition warning diode LED 2.

Figure 4:
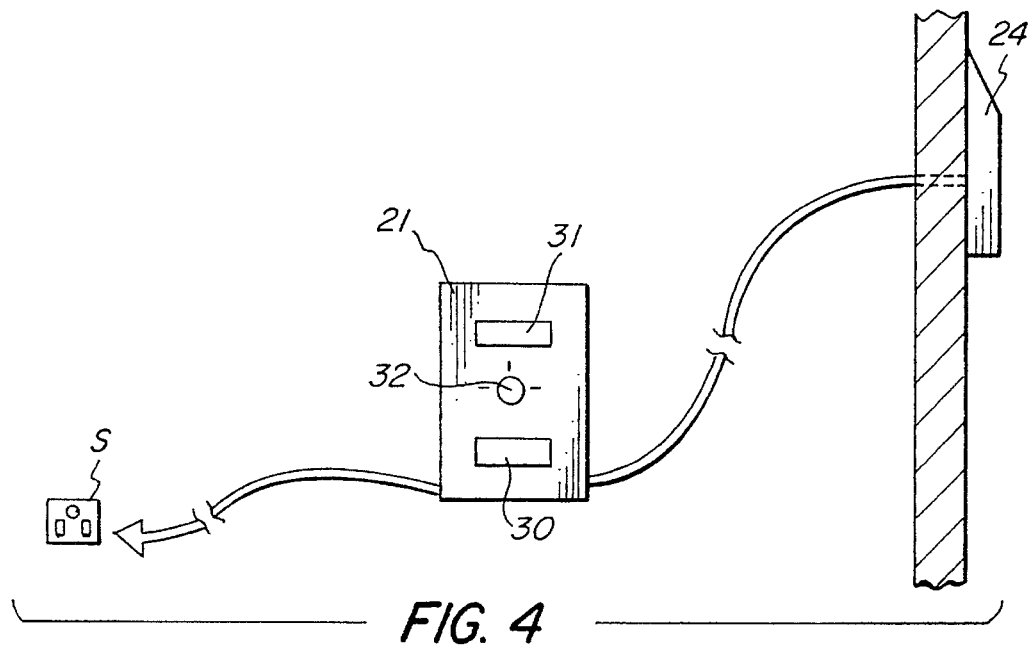
FIG. 4 is a general view of a control box and an alarm box for use with the signalling device.
Figure 5:
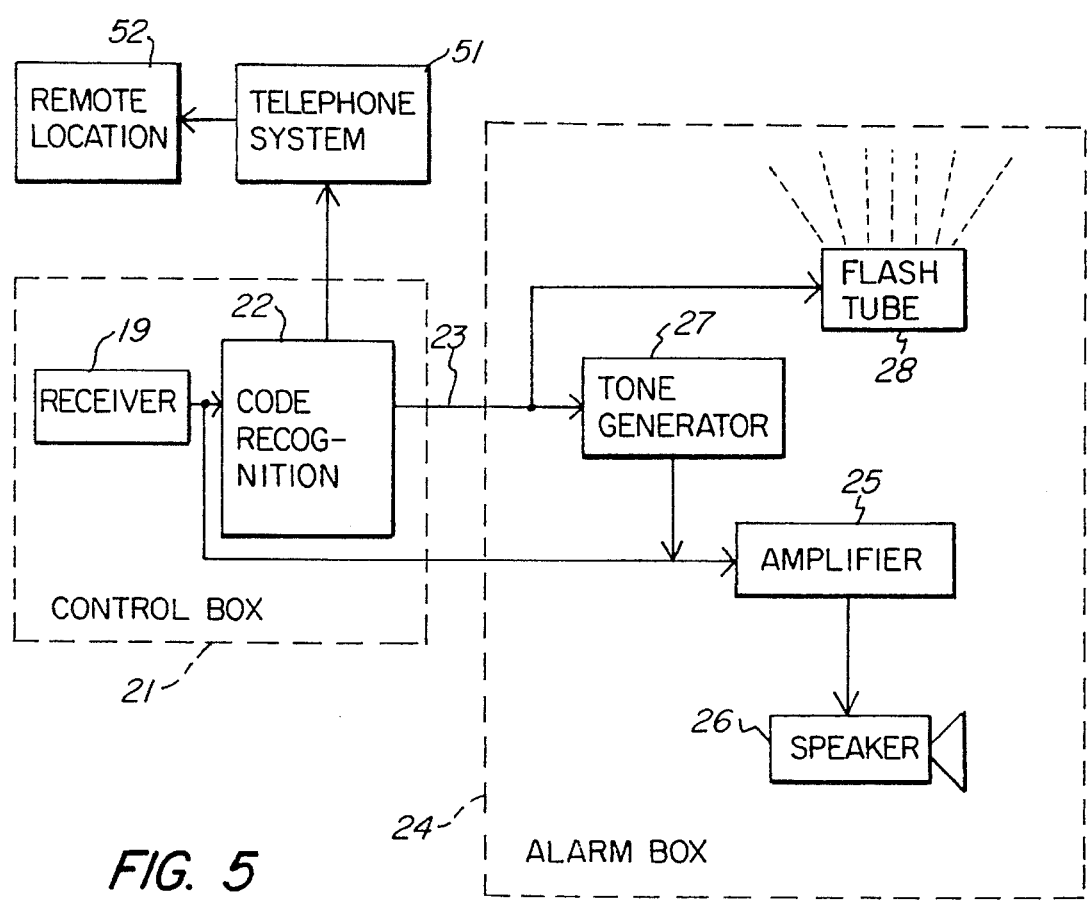
FIG. 5 is a block circuit diagram of the alarm and control boxes.

Referring now to FIGS. 4 and 5, the signals sent out by the signalling device 41 are picked up by a receiver 19 mounted in the control box 21. The control box may be mounted in a convenient location inside the building, powered either direct from the mains or via a mains socket S, with the back-up of rechargeable batteries in the event of a mains power failure. The receiver 19 demodulates the audio signals received from the transmitter 14 (IC3) and also sends the coded signals which it receives to a code recognition circuit 22. Recognition of an appropriately coded signal results in the generation of an alarm signal at 23. The control box is hard-wired to an alarm box 24 mounted on the outside of a building. The alarm box contains rechargeable batteries (not shown) which are powered from the control box 21, together with an audio amplifier 25 which feeds a loudspeaker 26. The audio amplifier 25 is driven by an audio tone generator 27 which is activated by the alarm signal from the control box. The alarm signal also activates a xenon flasher tube 28 mounted in the alarm box. The amplifier also receives the demodulated audio signals.

As well as allowing for re-charging the signalling device when rechargeable batteries are used, the signalling device can be provided with shift registers in place of the switch bank of FIG. 3B, which is programmed with the identification code from the control box, as noted above. The code can be entered into the control box by the user by means of a set of external miniature switches or a keypad 31. The code is automatically transferred to the shift registers of the signalling device each time the device is placed in the cradle 30. This allows the user to set his own identification code. Alternatively, the code can be pre-programmed into the control box at point of manufacture by internal miniature buttons, links or switches mounted on an internal printed circuit board. In this case the same code must be pre-programmed into the signalling device at point of manufacture, and it will not therefore be necessary to transfer the code via the cradle.

The control box may also incorporate a 3-digit, 7 segment led display 31. A keypad or three position key switch 32 is provided on the control box 21 to place the system into an ARM, RESET or TEST mode. In the ARM mode the display 31 could show the message SET to indicate that the system has been set ready for use, and in the RESET mode the message "rES" is displayed to show that the system is in a reset state, i.e. inactive. When the system is in the TEST mode the digital display on the control box indicates "tES". If the emergency button 2 is now depressed the display will change to indicate the decimal value of the transmitted identification code, but the alarm box is not activated. This is useful in setting up the system and in fault finding. The test mode is terminated by selecting one of the other two modes. To test the alarm box the emergency button 2 should be depressed whilst the system is in the normal ARM mode, causing the system to be fully activated, as will now be described.

When the user depresses the alarm button 2 the transmitter 14 sends the coded signal for a period of approximately five seconds. During this time the coded signal is repeated some hundred or so times to reduce recognition errors. When the recognition circuit 22 responds to the code, it sends an alarm signal to the alarm box which activates the tone generator 27 so that a warning tone is emitted by the loudspeaker 26 for about seven seconds, and the xenon tube 28 also gives out a visual indication. The transmitter then switches to transmit voice signals from the microphone 3. The control box receives these signals and sends them to the alarm box 24 to be broadcast via the loudspeaker to the outside world.

If the control box detects silence for a period of fifteen seconds the audible alarm is generated for a further seven seconds. This sequence is repeated until the signalling device is placed in the cradle 22 and/or the keypad or key switch is placed in the "RESET" mode, which causes the alarm box to be deactivated.

Multiple slave alarm boxes and repeaters can be attached to one control box enabling the coded signal and voice transmissions to be received and broadcast over a large area.

The system could be interfaced to the public telephone network 51 (FIG. 5) via the control panel or the alarm box or by incorporating the receiver unit into a telephone console. Reception of the appropriate identification code could cause the console to generate selected preset of user-programmed telephone numbers. Thus, when the button 2 is depressed a designated remote monitoring base 52 can monitor voice transmissions directly from the user, enabling the base to initiate the appropriate emergency action with minimum time delay.

In order that the system may be interfaced to existing security systems a relay output (not shown) is provided. The system is also designed to interface with compatible accessories. The control box can incorporate a standard cassette tape recorder for recording the audio signals to help trace and convict aggressors for example.

The equipment described could for example be installed in the home of an elderly person. The reproduction of audio signals by the external speaker will alert neighbours or passers by that the occupier requires assistance. This acts to reassure the user that if they should come face to face with an aggressor their cries of help will be heard. People also tend to react quicker to cries of help than they do to an alarm bell or siren.

By using a number of signalling units with different identification codes a number of individuals can be simultaneously monitored, in a nursing home or hospital for example. A separate monitoring unit could be sited on each floor of a residential nursing home, the unit having a panel with audible and/or visual indicators to indicate where each of the monitored people is located on that particular floor. A portable hand held receiver and alarm could be used instead of the fixed alarm and control box.

I claim:

1. An alarm system which includes an alarm signalling device comprising a housing (1) adapted to be worn on the person, the alarm signalling device including:

transmitter means (14) for sending out radio signals, a microphone (3) for picking up sounds and producing audio signals to modulate said transmitter means, emergency trigger means (2) for operating the transmitter means (14), and code generator means (16) for modulating the transmitter means with an encoded identification signal, said transmitter means, said microphone, said trigger means and said code generator means being operatively interconnected, and said transmitter means (14) being constructed to transmit, for an initial period, encoded information from said code generator means (16), and to thereafter switch automatically to transmit said audio signals for a second period.

2. An alarm system according to claim 1, in which said transmitter means (14) is constructed to repeatedly transmit the encoded identification signal during said initial period.

3. An alarm system according to claim 1, including control means (21) which comprises radio receiver means (19) for receiving and demodulating said radio signals sent out by said transmitter means (14), and a recognition circuit (22) for generating an alarm signal when the correct encoded identification signal is received, the alarm signal being arranged to operate audible (26) and/or visual (28) alarm means, and the receiver means (19) being arranged to send said audio signals to loudspeaker means (26).

4. An alarm system according to claim 3, in which said control means is constructed to operate the alarm means for periods which alternate with intermediate periods in which said audio signals drive the loudspeaker means (26).

5. An alarm system according to claim 1, including control means which comprises radio receiver means and a recognition circuit for initiating a telephone call to a remote location via a telephone system when the correct encoded identification signal is received the control means being arranged to feed said audio signals to the remote location via the telephone system.

6. An alarm system according to claim 1, including control means (21) for storing an identification code and including connection means (30) for transferring the identification code to the signalling device, said signalling device including store means (17) for storing the received identification code.

7. An alarm system according to claim 6, in which the control means (21) is arranged to permit the user to enter the identification code into the control means.

* * * * *